United States Patent
Potyrailo et al.

(10) Patent No.: US 6,608,678 B1
(45) Date of Patent: Aug. 19, 2003

(54) SITU DETERMINATION OF DPC AND BPA IN POLYCARBONATE BY RAMAN SPECTROSCOPY

(75) Inventors: Radislav Alexandrovich Potyrailo, Niskayuna, NY (US); Ronald Eugene Shaffer, Clifton Park, NY (US); Patrick Joseph McCloskey, Watevliet, NY (US)

(73) Assignee: General Electric Company, Niskayuna, NY (US)

( * ) Notice: Subject to any disclaimer, the term of this patent is extended or adjusted under 35 U.S.C. 154(b) by 364 days.

(21) Appl. No.: 09/692,549

(22) Filed: Oct. 19, 2000

(51) Int. Cl.[7] .............................. G01J 3/44; G01N 21/65
(52) U.S. Cl. ....................................... 356/301
(58) Field of Search ......................... 356/301

(56) References Cited

U.S. PATENT DOCUMENTS

| | | | |
|---|---|---|---|
| 4,620,284 A | | 10/1986 | Schnell et al. |
| 5,139,334 A | | 8/1992 | Clarke |
| 5,262,644 A | * | 11/1993 | Maguire ............... 356/301 |
| 5,455,673 A | | 10/1995 | Alsmeyer et al. |
| 5,638,172 A | | 6/1997 | Alsmeyer et al. |
| 5,652,653 A | | 7/1997 | Alsmeyer et al. |
| 5,999,255 A | * | 12/1999 | Dupee et al. ............ 356/301 |
| RE36,529 E | * | 1/2000 | Lewis et al. ............ 356/301 |

FOREIGN PATENT DOCUMENTS

| | | | |
|---|---|---|---|
| WO | WO - 99/27350 | * | 6/1999 |
| WO | WO - 00/49395 | * | 8/2000 |

OTHER PUBLICATIONS

Adar, F. et al., "Raman Process Analyzers Allow Rapid Online Control," *InTech*,.44:57–59 (Jul. 1997).
Adar, F. et al., "Raman Spectroscopy for Process/Quality Control," *Appl. Spectro. Rev.* 32(1&2) 45–101 (1997).
Al–Khanbashi, et al., Application of In–Line Fiber–Optic Raman Spectroscopy to Monitoring Emulsion Polymerization Reactions, *Appl. Spectro. Rev.* 33(1&2) 115–131 (1998).
ASTM E 1655–97, Standard Practices for Infrared, Multi-variate, Quantitative Analysis; ASTM: (1997).
Beebe, K.R., et al., In *Chemometrics: A Practical Guide*, Wiley, pp. 5, 46–49 and 90–99, (1998).
Boghosian, S., et al., "Determination of Stoichiometry of Solutes in Molten Salt Solvents by Correlations of Relative Raman Band Intensities," *Appl. Spectrosc.* 53:565–571 (1999).
Everall, N. et al., "Performance Analysis of an Integrated Process Raman Analyzer Using a Multiplexed Transmission Holographic Grating, CCD Detection, and Confocal Fiber–Optic Sampling," *Appl. Spectrosc.*, 49(5) 610–15 (1995).
Everall, N. et al., "Raman Spectroscopy for Polymer Characterization in an Industrial Environment," *Macromol. Symp.*, 141:103–116 (1999).
Ewing, K.J. et al., "Monitoring the Absorption of Organic Vapors to a Solid Phase Extraction Medium. Applications to Detection of Trace Volatile Organic Compounds by Integration of Solid Phase Absorbents with Fiver Optic Raman Spectroscopy," *Anal. Chim. Acta* 340:227–232 (1997).

(List continued on next page.)

Primary Examiner—F. L. Evans
Assistant Examiner—Kara Geisel
(74) Attorney, Agent, or Firm—Noreen C. Johnson; Christian G. Cabou

(57) ABSTRACT

The present invention provides a method for monitoring a reaction mixture using Raman spectroscopy. In a preferred embodiment, the invention provides a method for monitoring bulk and thin film melt polycarbonate polymerization reactions. In this method, the relative and absolute concentrations of the starting materials diphenylcarbonate (DPC) and bisphenol-A (BPA) are determined. Monitoring and maintenance of optimum stoichiometry in such a reaction is critical to ensuring desired polycarbonate product quality.

70 Claims, 11 Drawing Sheets

OTHER PUBLICATIONS

Ewing, K.J. et al., "Detection of Low Levels of Trichloroethylene Vapor With Raman Spectrometry," *Appl. Opt.* 33:6323–6327 (1994).

Huy, N. et al., "Application of Partial Least–Squares Regression to Remote Quantitative Analysis by the Raman–Laser—Fibre–Optics (RLFO) Method," *Analysis* 20:141–147 (1992).

Ingle, J.D. Jr. et al., In *Spectrochemical Analysis*; Prentice Hall, Englewood Cliffs, NJ, p. 8, (1998).

Lewis, I.R. et al., "Raman Spectrometry with Fiber–Optic Sampling," *Appl. Spectrosc.* 50(10):12A–30A (1996).

Niemczyk, T.M., et al., "Multichannel Raman Spectroscopy Tackles Industrial Problems," *Laser Focus World*, 85–98 (Mar. 1993).

Shaffer, R.E., et al. "Software for Generating Synthetic Passive Fourier Transform Infrared Interferograms and Single–Beam Spectra," *NRL Memorandum Report*, 6110–99–8342, pp. 1–58, (1999).

Shaffer, R.E., et al. "Signal Processing Strategies for Passive FT–IR Sensors," *Proc. SPIE–Int. Soc. Opt. Eng.*, 3383:92–103 (1998).

Shaffer, R.E. et al, "Genetic Algorithm Based Protocol for the Coupling of Digital Filtering and Partial Least Squares Regression: Application to the Near–Infrared Analysis of Glucose in Biological Matrices," *Anal. Chem.* 68:2663–75 (1996).

Sherman, R.E., In *Analytical Instrumentation: Practical Guides for Measurement and Control*; Instrument Society of America, Research Triangle Park, NC, p. 528, (1996).

\* cited by examiner

SITU DETERMINATION OF DPC AND BPA IN POLYCARBONATE BY RAMAN SPECTROSCOPY

BACKGROUND OF THE INVENTION

This invention relates to a nondestructive methodology for rapid measurement of reaction components in polymerization reactions. In particular, this method describes Raman spectroscopy for quantitation of diphenylcarbonate (DPC) and bisphenol-A (BPA) in polycarbonate melt polymerization reactions.

The stoichiometry of reaction components, such as monomers, solvents and reaction byproducts, can be manipulated during the course of a reaction to influence the final characteristics of the polymer produced. For example, the stoichiometry of polycarbonate monomers such as diphenylcarbonate (DPC) and bisphenol-A (BPA) is important in the production of high quality melt prepared melt polycarbonate resin. Monomer stoichiometry strongly influences polymerization rate, which, in turn, determines the amount of catalyst added and the amount of Fries rearrangement products formed. In addition, monomer stoichiometry determines final polycarbonate endcap levels. Variability in the DPC/BPA stoichiometry, therefore, directly translates into variability in the polycarbonate product.

Thus, for many reactions, it is necessary to monitor the stoichiometric proportions of the various reactants in order to ensure high quality product. In some cases, this may require numerous measurements over a short period of time.

Conventional techniques for monitoring polymerization reactions generally involve analyzing aliquots from the reaction mixture by methods such as liquid chromatography and/or Fourier Transform IR spectroscopy. These and other methods of laboratory analysis, however, are often time consuming, generate additional waste, and for high temperature or high pressure reactions, sampling of materials for laboratory analysis can be dangerous. Also, removing aliquots may alter the reaction conditions or sample constitution, and provides only temporally discrete data points, rather than a continuous profile. Alternatively, samples may be analyzed after the reaction is complete, and unsatisfactory products discarded. Post-reaction sampling, however, does not enable real-time optimization of reaction parameters and, therefore, may result in the synthesis of a polymer batch of substantially inferior quality.

Also, reaction conditions are generally optimized on a smaller scale than used in production. For example, since its introduction in 1970, combinatorial chemistry has become a popular research tool among scientists in many fields. There has been, however, a lag in the development of combinatorial screening for production scale reactions. One reason has been the difficulty in emulating large-scale reactions at the micro-scale necessary for combinatorial work. Another difficulty is that for many reactions, efficient methods of product analysis have yet to be developed. Moreover, methods applied to combinatorial libraries must carry over to analysis of the reaction on a commercial scale.

Therefore, there is a need for an on-line method for optimization of production scale polycarbonate synthesis. The method should eliminate the need for direct sampling and allow for the generation of continuous data. Also, the method should enable optimization of the overall melt prepared process and improve plant capability. Similarly, there is a continuing need to evaluate economically superior reactant systems. Thus, the method should be adaptable to combinatorial evaluation of new reactant and catalyst combinations, as well as production-scale reactant systems.

SUMMARY

The present invention is directed to a method for monitoring a reaction mixture using Raman spectroscopy. In one aspect, the invention provides a method for monitoring the process of polymer formation comprising irradiating a polymer with substantially monochromatic radiation; collecting a Raman spectrum corresponding to radiation scattered form the irradiated polymer; monitoring at least one wavenumber of the collected Raman spectrum; correlating the collected spectrum to at least one reaction component of interest; and applying a predetermined selection test to determine whether any one of a set of preselected reaction components needs to be adjusted.

In another aspect, the invention provides a method for monitoring the process of polycarbonate formation comprising irradiating a polymer with substantially monochromatic radiation; collecting a Raman spectrum corresponding to radiation scattered from the irradiated polymer; measuring the intensity of at least two preselected Raman bands; correlating the intensity of at least two preselected Raman bands to the stoichiometry of sample diphenylcarbonate (DPC) and bisphenol-A (BPA), and applying a preselected selection test to determine whether the input of DPC and BPA needs to be adjusted. Also included in the present invention are systems for performing the method.

Yet another aspect of the invention is an apparatus for performing methods of the invention comprising a light source which emits substantially monochromatic radiation to irradiate a polymer sample; a probe which transmits light from the light source to irradiate the polymer sample and collects radiation scattered from the irradiated polymer corresponding to a Raman spectrum; and a detector, wherein the detector monitors at least one wavenumber of the collected Raman spectrum which is correlated to at least one reaction component of interest.

BRIEF DESCRIPTION OF THE DRAWINGS

Various features, aspects and advantages of the present invention will become more apparent with reference to the following description, appended claims, and accompanying drawings, wherein:

DETAILED DESCRIPTION OF THE INVENTION

Figure 1:
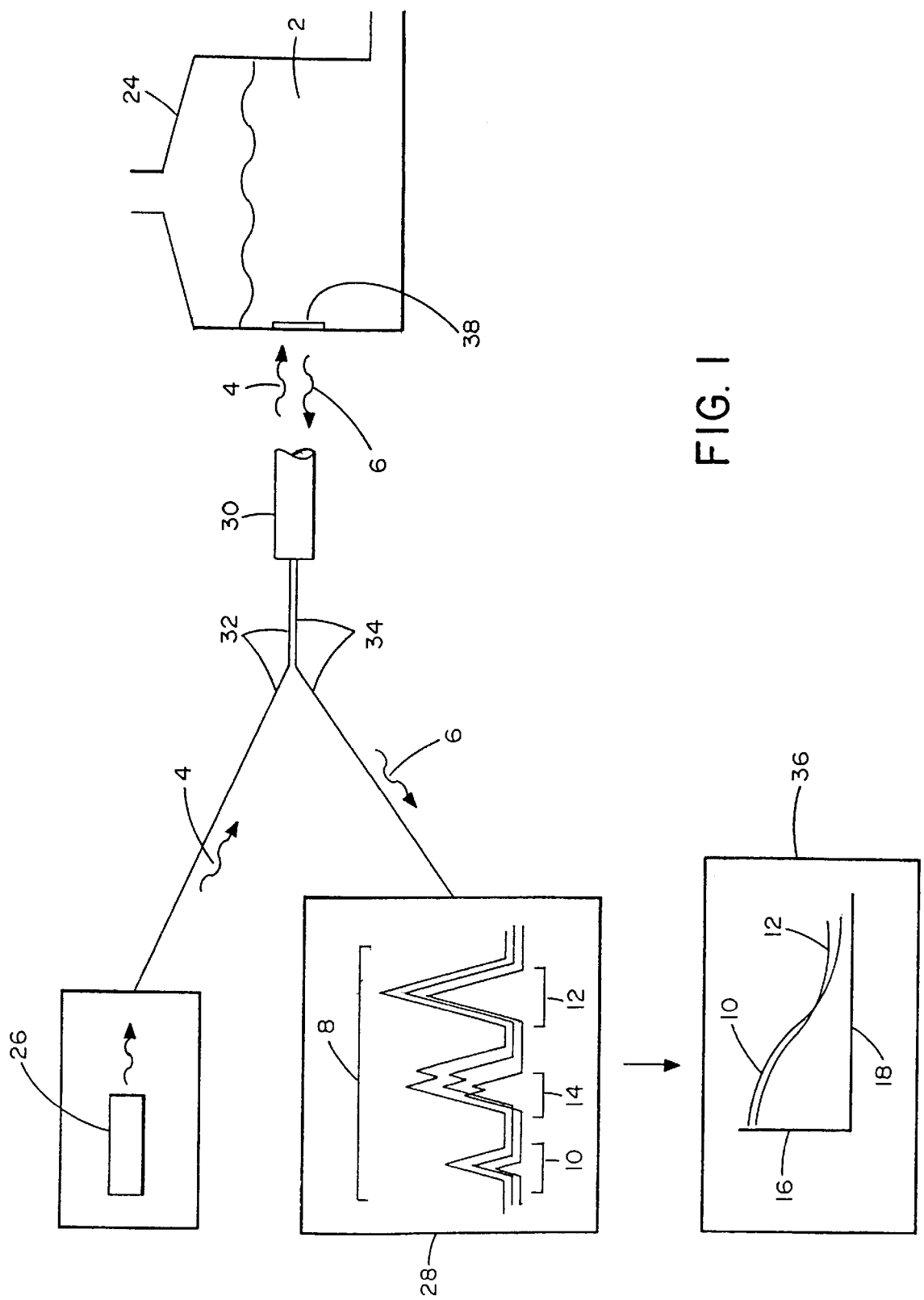
FIG. 1 is a representation of an aspect of an embodiment of the method and apparatus of the invention.

Terms used herein are employed in their accepted sense or are defined. In this context, the present invention is directed to methods and an apparatus for real-time/on-line monitoring of a polymerization reaction in situ, without the removal of aliquots for sampling. The present invention relates to the monitoring of reactions ranging in size from small scale combinatorial formats to production scale reactors.

In one aspect, the method relates to monitoring the process of polymer formation comprising irradiating at least one polymer with substantially monochromatic radiation; collecting a Raman spectrum corresponding to light scattered from the irradiated polymer; monitoring at least one wavenumber of the collected spectrum; correlating the monitored spectrum to at least one reaction component of interest; and applying a predetermined selection test to determine whether any one of a preselected set of reaction components needs to be adjusted.

Preferably, the polymer is melt polycarbonate. In an embodiment, the melt polycarbonate is solid. In an embodiment, the melt polycarbonate is molten. More Preferably, a reaction component of interest is diphenylcarbonate (DPC). Also more preferably, a reaction component of interest is bisphenol-A (BPA). Also more preferably, a reaction component of interest is phenol. Also more preferably, a reaction component of interest is polymer product.

In an embodiment, the method comprises monitoring the Raman spectrum at more than one wavenumber and correlating the Raman spectrum to the ratio of two reaction components of interest. More preferably, the two reaction components of interest comprise DPC and BPA. Also more preferably, the method comprises univariate analysis for quantitative prediction of the ratio of two reaction components of interest. Also more preferably, the method comprises multivariate analysis for quantitative prediction of the ratio of two reaction components of interest.

In an embodiment, the irradiating light comprises a wavelength in the range of about 400 to 1200 nm. More preferably, the irradiating light comprises a wavelength in the range of about 650 to 900 nm. Even more preferably, the irradiating light comprises a wavelength in the range of about 750 to 800 nm. Even more preferably, the irradiating light comprises a wavelength of about 785 nm.

In an embodiment, the collected spectrum comprises wavenumbers of about 50 to 5,000 $cm^{-1}$. More preferably, the collected spectrum comprises wavenumbers of about 200 to 3,500 $cm^{-1}$. Even more preferably, the collected spectrum comprises wavenumbers of about 400 to 3,000 $cm^{-1}$. Even more preferably, the collected spectrum comprises wavenumbers of about 500 to 2,000 $cm^{-1}$.

In an embodiment, the irradiation and collection of Raman spectra is performed on combinatorial libraries. Preferably, combinatorial libraries comprise multiple samples dispensed in an array such as a 96-well microtiter plate reactor.

In another aspect, the invention comprises a method for monitoring polycarbonate formation comprising irradiating at least one polymer with substantially monochromatic radiation; collecting a Raman spectrum corresponding to radiation scattered from the irradiated polymer; measuring the intensity of at least two preselected Raman bands; correlating the intensity of at least two preselected Raman bands to the stoichiometry of sample DPC and BPA; and applying a predetermined selection test to determine whether the input of DPC and BPA needs to be adjusted.

Preferably, the polymer is melt polycarbonate. In an embodiment, the melt polycarbonate is solid. In an embodiment, the melt polycarbonate is molten. More preferably, the method comprises univariate analysis for correlating the intensity of the preselected Raman bands to the stoichiometry of sample DPC and BPA. Also more preferably, the method comprises multivariate analysis for correlating the intensity of the preselected Raman bands to the stoichiometry of sample DPC and BPA.

In an embodiment, the irradiating light comprises a wavelength in the range of about 400 to 1200 nm. More preferably, the irradiating light comprises a wavelength in the range of about 650 to 900 nm. Even more preferably, the irradiating light comprises a wavelength in the range of about 750 to 800 nm. Even more preferably, the irradiating light comprises a wavelength of about 785 nm.

In an embodiment, the collected spectrum comprises wavenumbers of about 50 to 5,000 $cm^{-1}$. More preferably, the collected spectrum comprises wavenumbers of about 200 to 3,500 $cm^{-1}$. Even more preferably, the collected spectrum comprises wavenumbers of about 400 to 3,000 $cm^{-1}$. Even more preferably, the collected spectrum comprises wavenumbers of about 500 to 2,000 $cm^{-1}$.

In an embodiment, the irradiation and collection of Raman spectra is performed on combinatorial libraries of samples dispensed in an array such as a 96-well microtiter plate reactor.

In yet another aspect, the invention comprises computer readable media comprising software code for performing the methods of the invention.

Another aspect of the invention comprises an apparatus for the nondestructive monitoring of polymer formation comprising a light source, wherein the light source emits substantially monochromatic radiation to irradiate a polymer sample; a probe, wherein the probe transmits light from the light source to irradiate the polymer sample and collects radiation scattered from the irradiated polymer corresponding to a Raman spectrum; and a detector, wherein the detector monitors at least one wavenumber of the collected Raman spectrum correlated to at least one reaction component of interest.

Preferably, the polymer is melt polycarbonate. In an embodiment, the melt polycarbonate is solid. In an embodiment, the melt polycarbonate is molten. More preferably, the reaction component of interest is diphenyl-carbonate (DPC). Also more preferably, the reaction component of interest is bisphenol-A. Also more preferably, the reaction component of interest is polycarbonate product. Also more preferably, the reaction component of interest is phenol.

In an embodiment, the light irradiating the polymer sample has a wavelength in the range of about 400 to 1,200 nm. More preferably, the light irradiating the polymer sample has a wavelength in the range of about 650 to 900 nm. More preferably, the light irradiating the polymer sample has a wavelength in the range of about 750 to 800 nm. More preferably, the light irradiating the polymer sample has a wavelength of about 785 nm.

In an embodiment, the monitored spectrum has a wavenumber of about 50 to 5000 $cm^{-1}$. More preferably, the monitored spectrum has a wavenumber of about 200 to 3,500 $cm^{-1}$. More preferably, the monitored spectrum has a wavenumber of about 400 to 3,000 $cm^{-1}$. More preferably, the monitored spectrum has a wavenumber of about 500 to 2,000 $cm^{-1}$.

In an embodiment, irradiation and collection of Raman spectra is from a combinatorial library of samples arranged in a microtiter plate reactors or other array. In yet another embodiment, the apparatus comprises computer readable media software code.

Thus, the invention describes using Raman spectroscopy for on-line monitoring of the relative stoichiometry of reaction components. Raman spectroscopy is a non-invasive technique which can provide both qualitative and quantitative information about a chemical composition. Raman spectroscopy is based upon inelastic light scattering by molecules, where the energy difference between the incident radiation and the scattered radiation is referred to as a Raman shift. A plot of intensity of scattered light versus energy difference is a Raman spectrum. Generally, the difference in energy between an incident photon and the Raman scattered photon is equal to the energy of vibration of the scattering molecule. Thus, the Raman spectrum provides a fingerprint unique to the molecular vibrational modes inherent to the sample, where the intensity of the peaks relates to the number of molecules in a particular vibrational state. Because the energy of a vibrational mode depends on the intramolecular structure and intermolecular environment, Raman spectroscopy can identify individual components of chemical compositions being studied.

As a result of key instrumental advances, Raman process analyzers have evolved over the past decade from laboratory instruments to tools suitable for monitoring production scale reactions (Adar, F., et al., *InTech*, 44:57–59 (1997); Lewis, I. R., et al., *Appl. Spectrosc.*, 50:12A–30A (1996)). In contrast to IR spectroscopy, Raman spectroscopy is compatible with inexpensive and rugged optical materials, such as glass and quartz. Additionally, while near-IR measurements are often difficult to interpret, Raman measurements can be understood in terms of chemical and physical changes inherent to the composition being monitored (Everall, N., et al., *Appl. Spectrosc.*, 49:610–615 (1995); Everall, N., et al., *Macromol. Symp.*, 141:103–116 (1999)).

Process Raman spectrometers have been used for on-line monitoring of polymerization kinetics, polymer composition, degree of polymerization, extrusion, polymer characterization, and other industrial applications.(Everall, N. et al. (1999); Al-Khanbashi, A., et al., *Appl. Spectrosc. Rev.*, 33:115–131 (1998); Adar, F., et al., *Appl. Spectrosc. Rev.*, 32:45–101 (1997); Adar, F., et al., *InTech*, 44:57–59 (1997)). Also, U.S. Pat. Nos. 5,455,673, 5,652,653 and 5,638,172 describe methods and an apparatus for using a convolution function derived for a reference to adjust the convolved Raman spectrum of an unknown, thereby reducing variance which often results due to the conditions used for on-line, production-scale measurement. In addition, U.S. Pat. No. 5,139,334 describes a method and apparatus for collecting and comparing Raman peaks for specific hydrocarbons relating to octane rating in gasoline, and U.S. Pat. No. 4,620,284 describes an apparatus and method for collecting a Raman spectrum, and systematically comparing the spectrum to a computerized database to determine the identity of an unknown.

In one aspect, and referring to FIG. 1, the invention comprises an apparatus for the nondestructive monitoring of polymer formation comprising a light source 26 which emits a substantially monochromatic radiation 4 to irradiate a sample 2; a probe 30 wherein the probe 30 transmits light 4 from the light source 26 to irradiate the polymer sample 2 and collects radiation 6 scattered from the irradiated polymer 2; and a detector 28, wherein the detector 28 monitors at least one wavenumber 10 of the Raman spectrum 8 correlated to at least one reaction component of interest.

Preferably, the light source 26 is a laser or diode laser which has a power in the range of about 50 to 2,000 milliwatts. In an embodiment, substantially monochromatic radiation 4 from laser 26 is transmitted via at least one illuminating fiber 32, emitted by probe 30 to irradiate sample 2, and scattered radiation 6 collected by probe 30 and transmitted by at least one collecting fiber 34 to detector 28. Preferably, detector 28 comprises a CCD camera, or the like. Fiber optic probe 30 may be a standard fiber optic probe or a high temperature fiber-optic probe.

The apparatus may be used for the in situ monitoring of polymer samples which are constituents of a larger structure. Thus, irradiation and collection of Raman spectra of sample 2 may be performed using a viewing port 38 on reactor 24. Alternatively, the apparatus may be used for monitoring polymer samples which are combinatorial libraries of samples dispersed in a 96-well microtiter plate reactor or other type of array. The reaction component of interest may be any components which have a Raman band which can be distinguished from other bands in the spectrum, mathematically or visually. Thus, the apparatus may be used to monitor levels of starting components, such as bisphenol-A and diphenylcarbonate (DPC), or reaction products such as melt prepared polymer and phenol.

The wavelength of the irradiating light 4 may range from about 400 to 1200 nm. More preferably, the wavelength of the irradiating light 4 ranges from about 650 to 900 nm. Even more preferably, the wavelength of the irradiating light 4 ranges from about 750 to 800 nm. Even more preferably, the wavelength of the irradiating light 4 is about 785 nm.

The monitored spectrum 8 may have a wavenumber which ranges from about 50 to 5,000 $cm^{-1}$. More preferably, monitored spectrum 8 has a wavenumber ranging from about 200 to 3,500 $cm^{-1}$. More preferably, the monitored spectrum 8 has a wavenumber ranging from about 400 to 3,000 $cm^{-1}$. Even more preferably, the monitored spectrum 8 has a wavenumber ranging from about 500 to 2,000 $cm^{-1}$.

In one aspect, and referring to FIG. 1, the invention comprises a method for in situ monitoring of polymer formation comprising the steps of irradiating at least one polymer 2 with a substantially monochromatic radiation 4, collecting a Raman spectrum 8 of radiation scattered 6 from the irradiated polymer 2, monitoring at least one wavenumber 10, 12, 14 of the collected spectrum 8 as a function of time, and correlating the change in at least one wavenumber 10 of the collected spectrum to at least one reaction component of interest. Polymer 2 is preferably either solid or molten melt polycarbonate. In an embodiment, the method is used for monitoring a large scale reactor, and irradiation and collection of Raman spectra of sample 2 are done using a viewing port 38 on reactor 24. Alternatively, irradiation and collection of Raman spectra may be performed on combinatorial libraries of samples dispersed in a 96-well microtiter plate reactor or other type of array.

Figure 2:
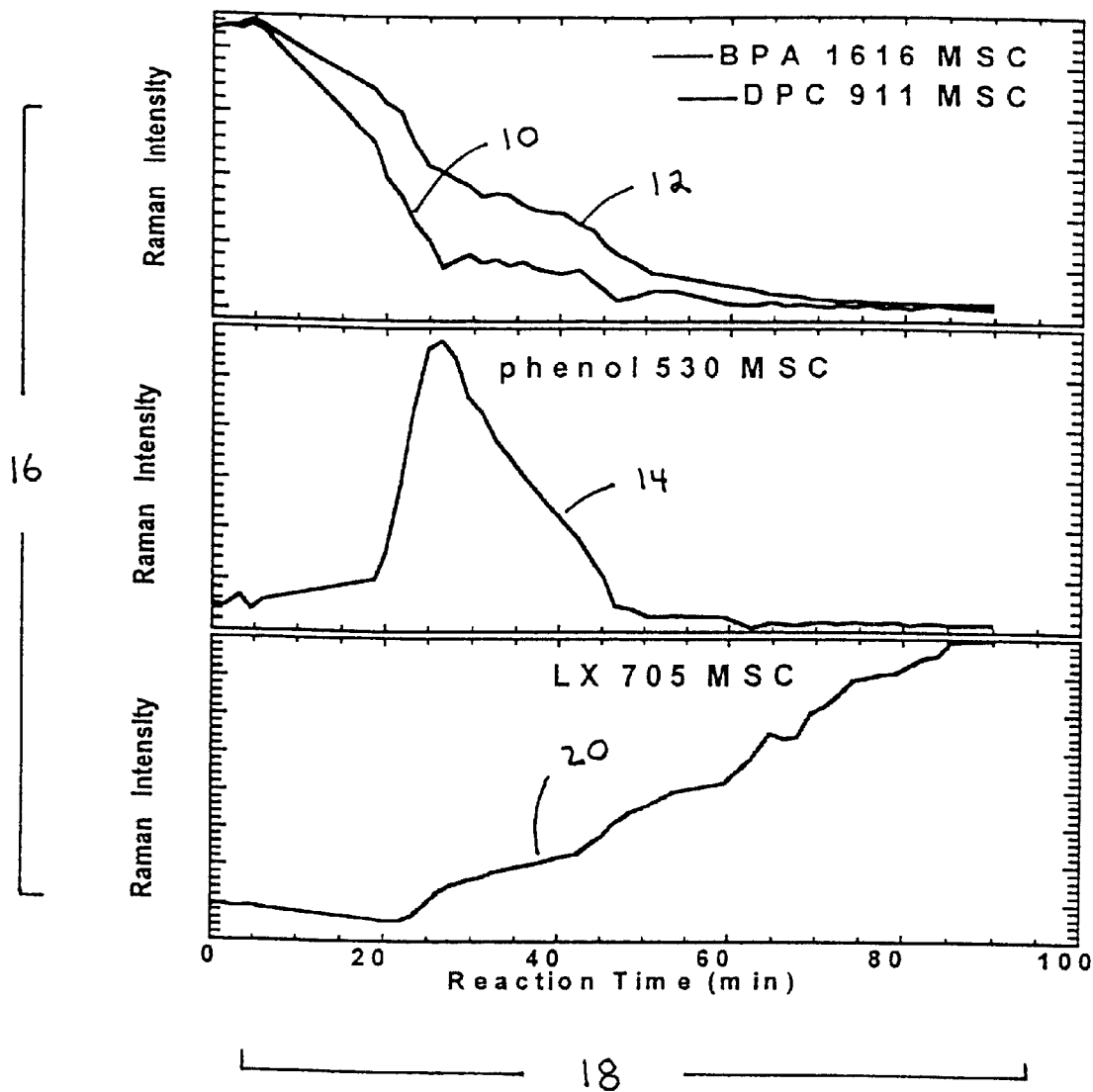
FIG. 2 illustrates an aspect of an embodiment of the invention comprising evolution of Raman intensities at indicated wavenumber positions corresponding to DPC, BPA, phenol and melt prepared polycarbonate as a function of reaction time.

In an embodiment, and referring now to FIGS. 1 and 2, the method is used to monitor the stoichiometries of reaction components during synthesis of melt polycarbonate. For example, the method may be used to measure the Raman intensities 16 corresponding to starting reactant monomers as a function of reaction time 18. Reaction components may be starting materials, such as DPC or BPA, in melt polymerization. Thus, the method of the invention is used to measure Raman peaks corresponding to DPC 10 or BPA 12 during the course of a polymerization reaction. Alternatively, the method is used to monitor reaction byproducts. Thus, the method is used to monitor a Raman peak corresponding to phenol 14 during melt transesterification. The method may also be used to monitor the formation of reaction products. Thus, the method is used to monitor the Raman peak 20 corresponding to melt prepared polymer formed during melt transesterification.

In an embodiment, the method of the invention comprises monitoring the ratio of band intensity of the Raman spectrum at two wavenumbers comprising two reaction components of interest. By taking a ratio, the measurement of band intensities is immune to variations which originate from process and instrumental sources. Such process variability includes, but is not limited to, sample temperature and viscosity. Instrument variability includes, but is not limited to, laser and detector instability. Preferably, the reaction being monitored is melt polycarbonate synthesis, and the reaction components of interest are DPC and BPA.

Figure 3:
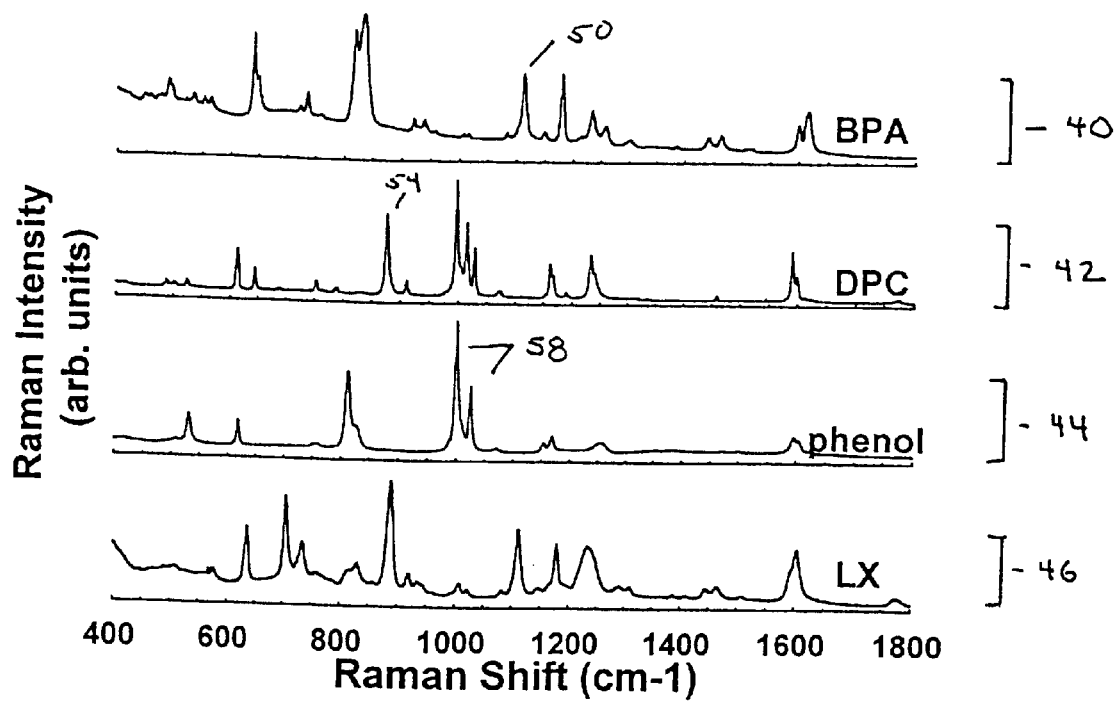
FIG. 3 illustrates an aspect of an embodiment of the invention comprising Raman spectra of melt prepared melt polymerization reaction components BPA, DPC, phenol and melt prepared product.

Thus, in an embodiment, the invention relates to the use of Raman spectroscopy for the determination of the stoichiometry of reaction components in bulk solid melt prepared oligomer. Once bands corresponding to reaction components of interest are identified, they can be monitored to follow the progress of the reaction. To determine appropriate spectral ranges for quantitative determinations of DPC and BPA, Raman spectra of DPC, BPA, phenol, and polycarbonate are compared to identify bands which are unique to the reaction components of interest. For analysis of DPC and BPA, Raman bands essentially distinct from phenol bands are identified. Referring to FIG. 3, bands used to identify reaction components can be identified from purified preparations of the components. For example, a Raman spectrum for BPA 40 is distinct from the Raman spectra for DPC 42, phenol 44, and melt prepared polymer 46, respectfully. In an embodiment, Raman bands can shift upon oligomerization of reaction components. Thus, the Raman spectra for purified reaction components are compared to the Raman spectra for the same components after oligomerization. Preferably, the bands will shift by a known amount, enabling identification of unique bands in the oligomer mixture correlated to the reaction components of interest. For example, in an embodiment, unique bands for BPA and DPC which are free from phenol are identified. Upon oligomerization, these bands shift to a predetermined position, but are still predominantly free of interference from phenol.

Figure 4:
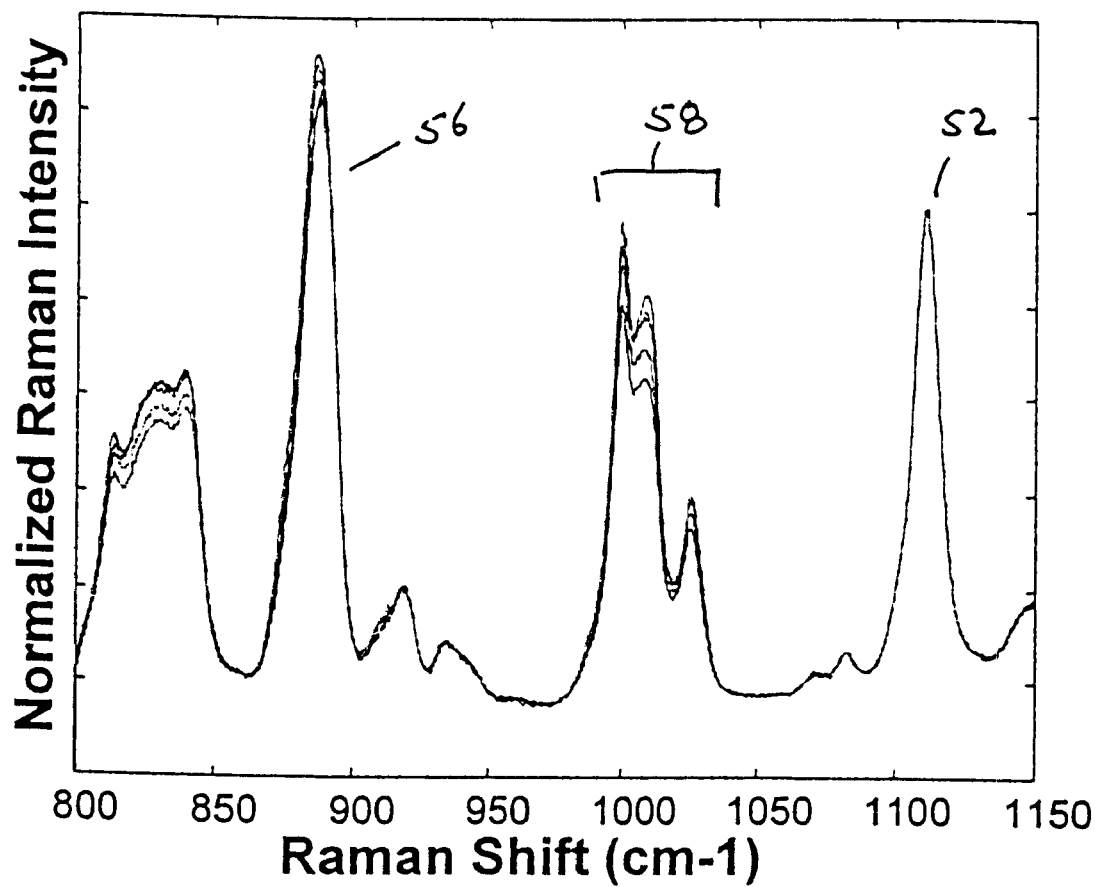
FIG. 4 illustrates an aspect of an embodiment of the invention comprising normalized spectra of solid melt prepared oligomers.

For example, in an embodiment and referring to FIGS. 3 and 4, band 50 at 1113 cm$^{-1}$ due to BPA (FIG. 3) shifts to 1111 cm$^{-1}$ 52 upon oligomerization (FIG. 4). Band 54 at 877 cm$^{-1}$ due to DPC (FIG. 3) shifts to 888 cm$^{-1}$ 56 upon oligomerization (FIG. 4). Bands due to non-oligomerized reaction components, such as phenol 58, are not strongly shifted upon oligomerization. Thus, in an embodiment, the BPA band at 1111 cm$^{-1}$ 52 and the DPC band at 888 cm$^{-1}$ 56, are not interfered with by spectral bands due to phenol 58.

Preferably, the light irradiating the polymer 2 comprises a wavelength in the range of about 400 to 1200 nm. More preferably, the light irradiating the polymer 2 comprises a wavelength in the range of about 650 to 900 nm. Even more preferably, the light irradiating the polymer 2 comprises a wavelength in the range of about 750 to 800 nm. Even more preferably, the light irradiating the polymer 2 comprises a wavelength of about 785 nm.

In an embodiment, the collected Raman spectrum comprises wavenumbers ranging from about 50 to 5,000 cm$^{-1}$. Preferably, the collected Raman spectrum comprises wavenumbers ranging from about 200 to 3,500 cm$^{-1}$. More preferably, the collected Raman spectrum comprises wavenumbers ranging from about 400 to 3,000 cm$^{-1}$. Most preferably, the collected Raman spectrum comprises wavenumbers ranging from about 500 to 2000 cm$^{-1}$.

Figure 5:
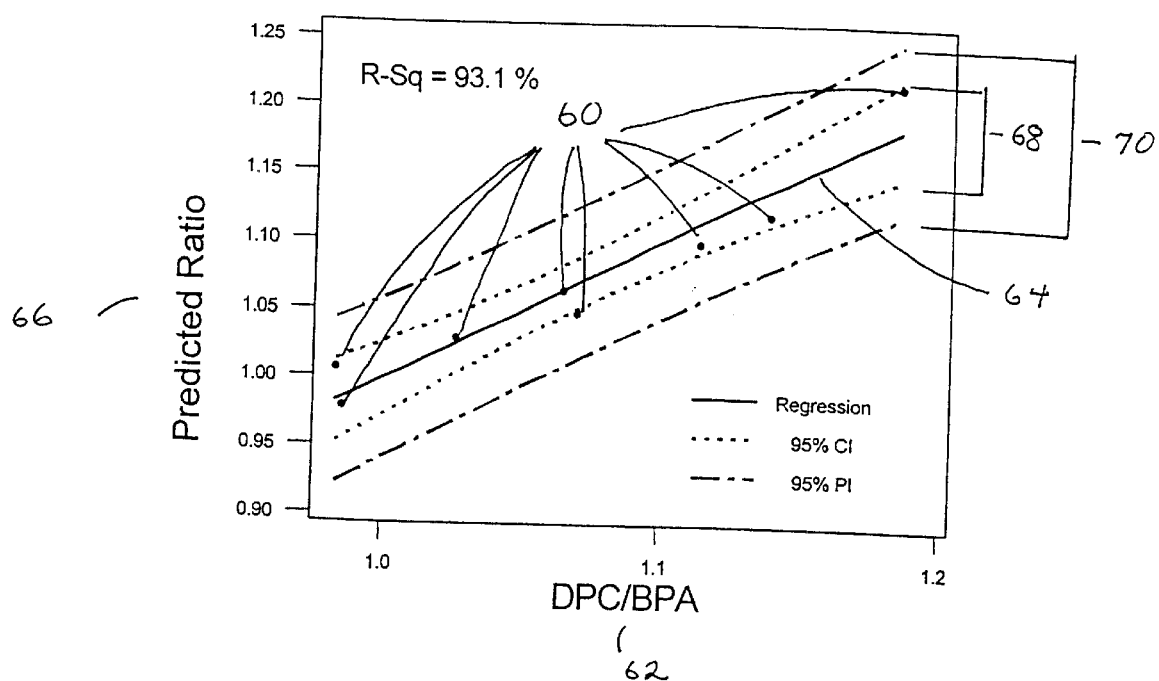
FIG. 5 illustrates an aspect of an embodiment of the invention comprising univariate calibration results for melt prepared oligomer samples utilizing the ratio of peak intensities of Raman bands at 888 $cm^{-1}$ and 1111 $cm^{-1}$.

The ratio of the intensities corresponding to reaction components of interest may be used for the development of a univariate calibration model to enable quantitative prediction of reaction components of interest. For melt polymerization, the reaction components of interest are BPA and DPC. Thus, in an embodiment, and referring to FIGS. 4 and 5, the ratio of Raman intensity at 888 cm$^{-1}$ 56 and 1111 cm$^{-1}$ 52 is taken for samples having a known DPC/BPA ratio 62. Measured values for the ratio of Raman intensity at 888 cm$^{-1}$ and 1111 cm$^{-1}$ ($I_{888}/I_{1111}$) 60 are plotted relative to the known values of the samples used 62, and a univariate model 64 for prediction of DPC/BPA ratios 66 generated. Preferably, a sufficient number of known samples is used to generate the model such that the 95% confidence interval 68 and the 95% prediction interval 70 are suitable for routine screening of polymer production.

Figure 6:
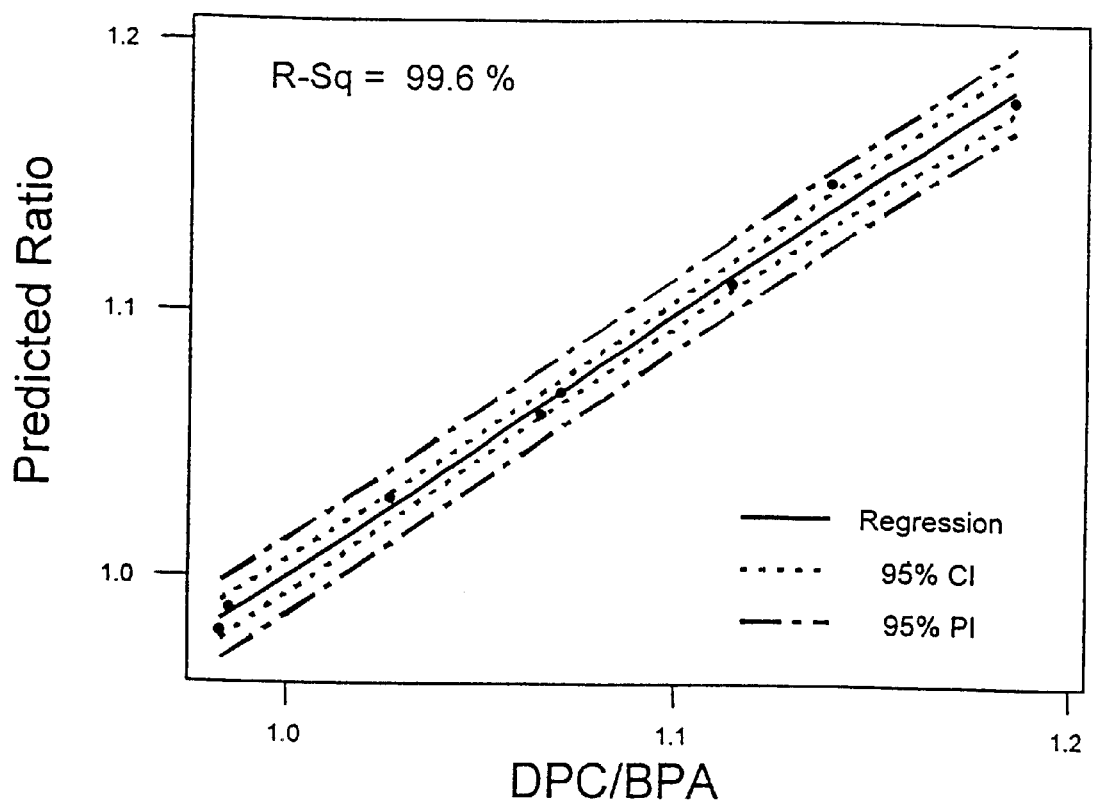
FIG. 6 illustrates an aspect of an embodiment of the invention comprising partial least squares regression (PLS) calibration results for solid melt prepared oligomer samples.

Alternatively, and referring now to, for example, FIG. 6, multivariate calibration methods, such as partial least squares regression (PLS) and the like, are used to correlate the Raman spectra to reaction components of interest. PLS calibration models have been used successfully for quantitative analysis in Raman spectroscopy (Everall, N., et al. (1995); Everall, N. et al., (1999); Adar, F. et al., *In Tech*, 57–59 (July 1997); Niemczyk, T. M., et al., *Laser Focus World*, March 1993, 85–98; Huy, N., et al., *Analysis* 20:141–147 (1992)), near-IR (Shaffer, R. E., et al., *Anal. Chem.* 68:2663–2675 (1996)) and FT-IR (Shaffer, R. E., et al., *Proc. SPIE-Int. Soc. Opt. Eng.*, 3383:92–103 (1998)). Generally, PLS models correlate the sources of variation in the spectral data with sources of variation in the sample. Given a large enough span of calibration samples, multivariate calibration models are generally more robust than univariate models due to enhanced outlier detection capabilities and increased tolerance toward slight shifting in peak position or band shape. Preferably, the sources of variation in the spectral bands correspond to reaction components of interest. For melt polymerization, the reaction components of interest preferably are DPC and BPA.

Thus, in an embodiment, PLS models the sources of variation in the spectral data that correlate with the sources of variation in the DPC/BPA ratio. To reduce computational requirements on the collected. Raman spectra, PLS modeling is preferably performed on spectra with reduced resolution. Spectral resolution is preferably reduced using methods such as that originally developed for FT-IR by Shaffer and Combs (Shaffer, R. E. et al., *NRL Memorandum Report* 6110:99–8342 (1999)). This method uses a combination of Fourier filtering and interpolation to produce data that resemble spectra collected on a lower resolution instrument. For the Raman spectra of melt prepared oligomers, the Fourier filtering step preferably helps to smooth the data and reduce noise. The filtered, low resolution Raman spectra can then be mean-centered prior to the PLS model building. Preferably, the PLS model is validated by statistical techniques. Such statistical techniques include, but are not limited to, leave one out cross-validation, venetian blinds, and random subsets (Beebe, K. R., et al., *Chemometrics: A Practical Guide*, Wiley, New York, N.Y. (1998)).

In an embodiment, the invention comprises determination of reaction components in solid polymers, such as melt prepared polycarbonate, and the like. The Raman spectrum for solid samples is sensitive to local variations in sample composition. Thus, for solid samples, measurements are preferably taken at three or more locations.

In an embodiment, the invention comprises determination of reaction components in molten polymers, such as melt prepared polycarbonate, and the like. Determination of reaction components in molten polymers preferably includes polymers ranging in temperature from about 180° C. to about 350° C. More preferably, determination of reaction components in molten polymers includes polymers ranging in temperature from about 210° C. to 320° C.

Figure 7:
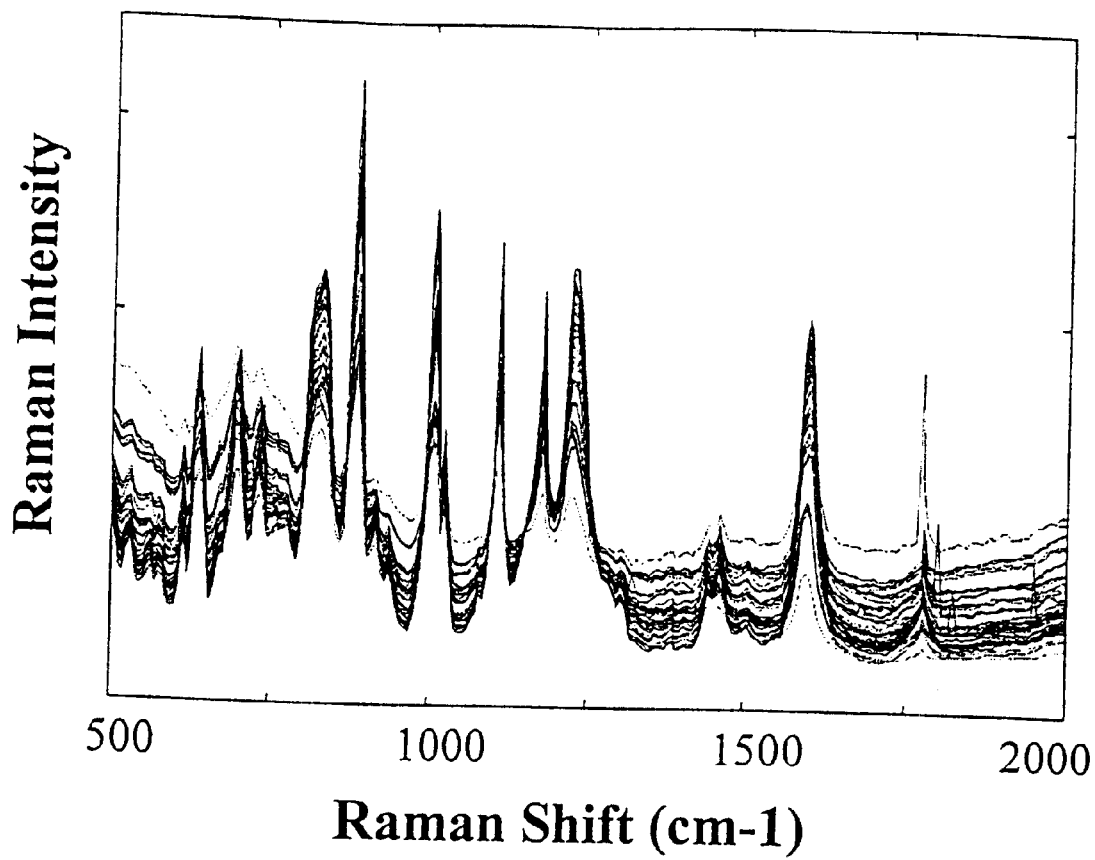
FIG. 7 illustrates an aspect of an embodiment of the invention comprising Raman spectra of molten polycarbonate samples preprocessed using a multiplicative scatter correction method.
Figure 8:
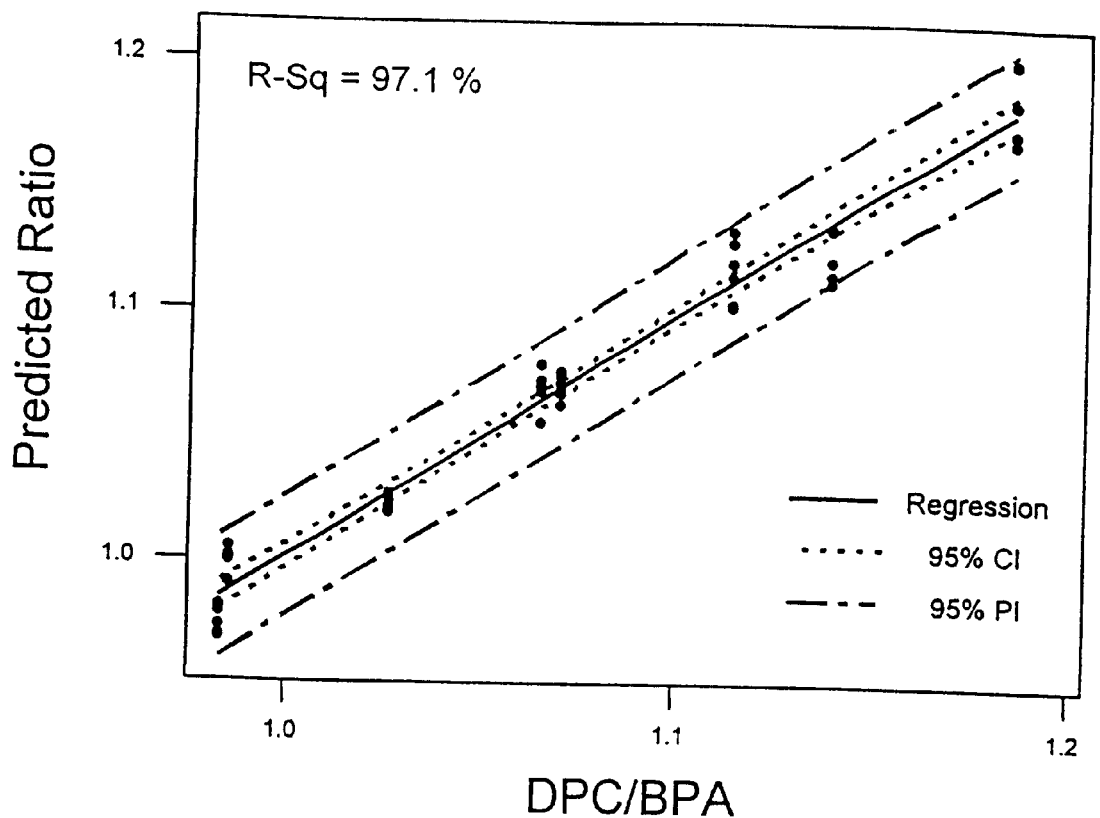
FIG. 8 illustrates an aspect of an embodiment of the invention comprising partial least squares regression (PLS) results for molten polycarbonate samples.

In an embodiment, and referring to FIGS. 7 and 8, quantitation of DPC/BPA in molten polycarbonate is performed using a standard fiber-optic Raman probe, such as probes supplied by Kaiser Optical Systems, Inc. (Ann Arbor, Mich.), InPhotonics, Inc. (Norwood, Mass.), Renishaw plc (New Mills, Wotton-under-Edge, Gloucestershire, United Kingdom), and the like. The use of a standard probe is possible by positioning the probe at some distance from the heated reactor surface. Generally, probes are about 3 mm, but not more than 200 mm, from the reactor surface. As will be understood by those of ordinary skill in the art, in the plant environment, it may be necessary to secure the probe in some type of retaining device that is heated to the same temperature as the reaction mixture flow, such as a flange or the like.

Figure 9:
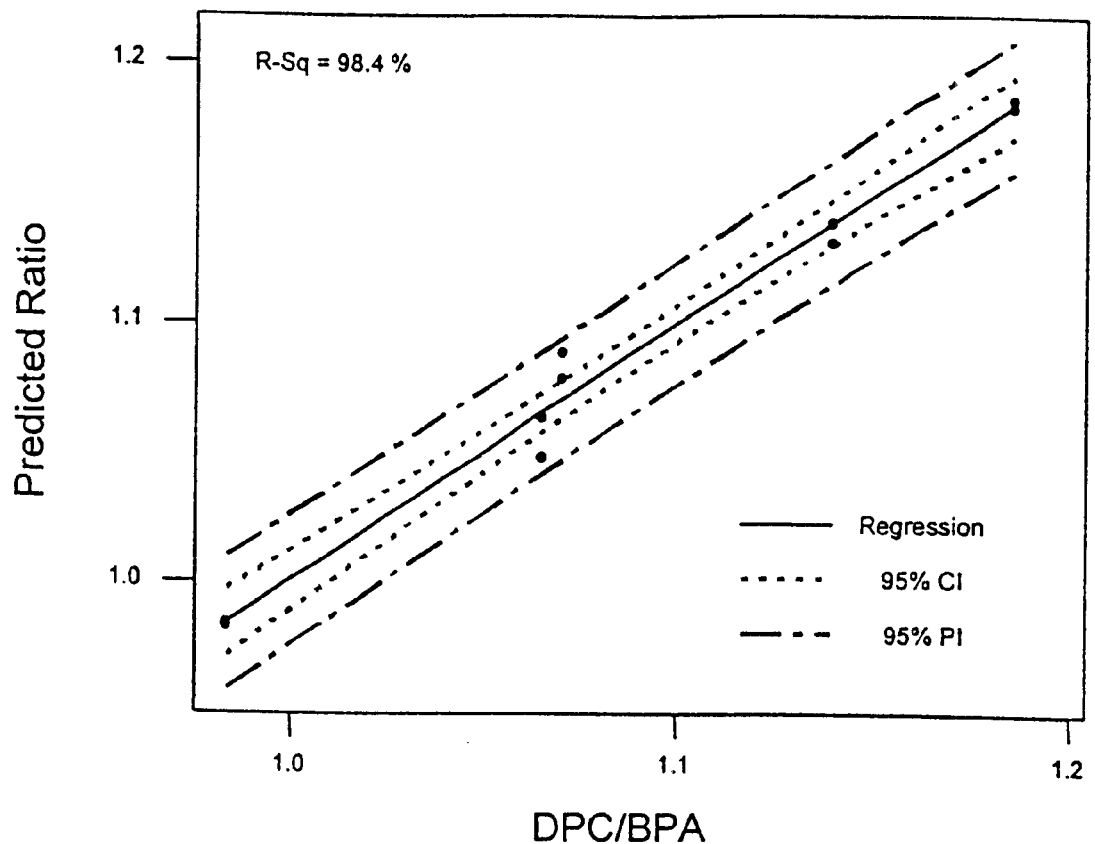
FIG. 9 illustrates an alternative aspect of an embodiment of the invention comprising partial least squares regression (PLS) results for molten samples.

In an embodiment, and referring now to FIG. 9, quantitation of DPC/BPA is performed using a high temperature fiber-optic Raman probe such as probes supplied by Kaiser Optical Systems, Inc. (Ann Arbor, Mich.), InPhotonics, Inc. (Norwood, Mass.), and the like. High temperature probes may be positioned closer to the reactor to deliver increased amounts of light to the sample, thereby increasing the quality of Raman spectra collected. Generally, an increase in probe integration time increases the signal-to-noise ratio, thereby allowing for accurate measurement of reaction components. In an embodiment, an integration time of about 5 seconds enables the necessary signal-to-noise ratio for determination of DPC/BPA ratios. Alternatively, the high temperature probe may be immersed directly in the sample.

In an embodiment, the PLS regression vector derived from the Raman spectra contains information for interpretation of reaction chemistry. Spectral regions that have a strong effect on the calibration model comprise larger regression coefficients, and the direction of the coefficient, positive or negative, provides an indication of whether a spectral region results in an increase or decrease, respectively, in specific reaction components. Thus, the PLS regression vector preferably provides an indication of whether a spectral region results in an increase or decrease in DPC/BPA ratio.

Figure 10:
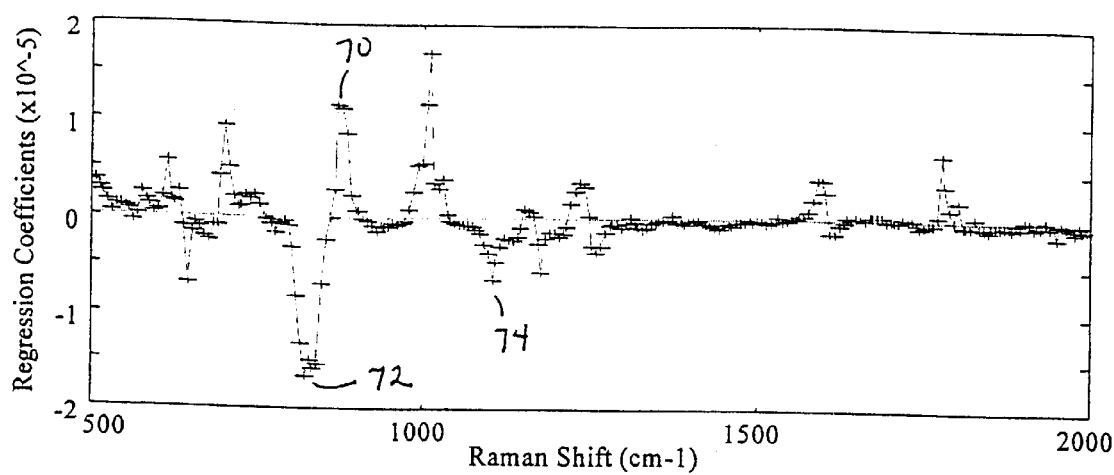
FIG. 10 illustrates a partial least squares regression (PLS) vector for molten polycarbonate samples.

Thus, in an embodiment, and referring now to FIG. 10, strong positive regression coefficients 70 can be found at ~888 $cm^{-1}$ which coincides with a strong Raman band for DPC. Strong negative coefficients 72 at ~835 $cm^{-1}$ are apparently due to both phenol and BPA. The 1111 $cm^{-1}$ spectral band from BPA also has a large negative coefficient 74. Because BPA contributions provide negative coefficients and DPC contributions are primarily positive, an increase in intensity for spectral regions related to DPC results in a larger DPC/BPA ratio. Conversely, a decrease in intensity in the (negative) BPA regions results in a decrease in the DPC/BPA ratio.

Preferably, interfering substances are corrected for mathematically by the calibration method used. For example, where melt prepared polycarbonate production is monitored, phenol is a primary interference, and characterization of Raman spectra preferably accounts for the Raman profile due to phenol. Interfering substances are preferably corrected for in the univariate analysis by selecting spectral regions in which the contribution of the interfering substance is minimal. In an embodiment, univariate analysis utilizes regions of the spectra, 888 $cm^{-1}$ and 1111 $cm^{-1}$, for DPC and BPA, respectfully, which are relatively free of signal due to phenol. Preferably, multivariate analysis implicitly subtracts out the contribution from interfering substance. Thus, in an embodiment, PLS implicitly subtracts out the contribution due to phenol.

As will be recognized by those of ordinary skill in the art, all or part of the steps in the method of the present invention may be coded or otherwise written in computer software, in a variety of computer languages including, but not limited to, C, C++, Pascal, Fortran, Visual Basic, Microsoft Excel, MATLAB, Maple, Mathematica, and Java. Accordingly, additional aspects of the present invention include computer software for performing one or more of the method steps set forth herein. The software code may be compiled and stored in executable form on computer readable media as, for example, computer rom, floppy disk, optical disk, hard disks, CD rom, or the like.

For example, an embodiment of a system for performing the methods of the invention comprises a discrete unit which includes a light source connected to a monochromator and a probe for irradiation via a viewing port of polycarbonate which is being generated in a large reactor. By monitoring Raman spectrum of light scattered, determining the $I_{888}/I_{1111}$ intensity ratio, and comparing the measured value to the model developed for that polymer, the operator is provided with a quantitative estimate of the ratio of DPC/BPA for the reaction. Based on the data, the operator may take steps to adjust the reaction mix. The entire system, or any part of the system, can be controlled by a computer and software specifically designed to implement a particular embodiment of the method. Thus, any and all steps of the method, including, but not limited to, irradiation of samples, collection of Raman spectra, collating processing of the data, statistical analysis, and adjustment of the reaction mix, may be specifically programmed and controlled by a computer.

EXPERIMENTAL SECTION

Features and advantages of the inventive concept covered by the present invention are illustrated in the following examples. The following materials and methods were utilized in the examples described herein.

Melt prepared oligomers were prepared in a 1 liter lab reactor. The reactor was charged with 0.6570 mol solid bisphenol-A (General Electric Plastics, Japan Ltd.) and 0.7096 mole solid diphenyl carbonate (General Electric Plastics, Japan Ltd.) prior to assembly. After assembly, the reactor was sealed and the atmosphere exchanged with nitrogen three times. With the final nitrogen exchange, the reactor was brought to near atmospheric pressure, and submerged into a fluidized bath at 180° C. After five min, agitation at 250 rpm was begun. After 10 min of agitation, the reactants were fully melted to form a homogeneous mixture. Tetramethyl ammonium hydroxide (TMAH) ($1.32 \times 10^{-4}$ mol; Sachem USA, Austin Tex.) and sodium hydroxide (NaOH) ($5.0 \times 10^{-7}$ mol; J. T. Baker, Phillipsburg, N.J.) were added sequentially as solutions of 220 mM TMAH and 5 mM NaOH diluted in 18 Mohm water. After the final addition of catalyst, the temperature was ramped to 210° C. over a five minute period. Upon reaching reaction temperature, the pressure was reduced to 180 mm Hg and the phenol distillate was immediately formed. After 25 min, the pressure was reduced to 100 mm Hg and the reaction maintained at this pressure for 45 min. The temperature was then ramped to 240° C. over a 5 min period, and the pressure reduced to 15 mm Hg. The reaction was maintained at these conditions (240° C. and 15 mm Hg) for an additional 45 min.

The materials obtained were then used for stoichiometry determination. Because there is some loss of BPA and DPC during the oligomerization process, stoichiometry was corrected. For Raman analysis, the value used for the "theoretical" stoichiometry was the stoichiometry after correction. The extent of monomer loss was quantified by HPLC analysis of the distillate and assumed to be the only loss of monomer. Corrected values for DPC/BPA ratios were in the range of 0.983 to 1.185 and are shown in Table 1.

TABLE 1

| Reaction ID# | Corrected DPC/BPA Ratio |
|---|---|
| 1442 | 0.983 |
| 1443 | 1.026 |
| 1444 | 1.070 |
| 1445 | 1.114 |
| 1446 | 1.139 |
| 1472 | 0.985 |
| 1473 | 1.065 |
| 1474 | 1.185 |

For measurements of a molten oligomer, ~0.1 g of material was heated in a quarts vial to 210° C. under a 250 cc per min flow of nitrogen. Heating was done with a temperature controller (Cole Parmer, Vernon Hills, Ill.).

Raman spectra measurements were performed using a fiber-optic Raman system that consisted of a spectrograph, a laser, and a fiber-optic probe. The Raman spectrograph (model Echelle-NIR775, EIC Raman Systems, Norwood, Mass.) covered a spectral range from 200 to 3500 cm$^{-1}$ with a 4-cm$^{-1}$ resolution. This capability was available by using a gold-coated echelle grating (52.65 lines/mm) that dispersed light in two dimensions to fully exploit the CCD detector area. The detector was a Photometrics Inc., (Tucson, Ariz.) CH270 cryogenically cooled CCD camera. The light source was a wavelength-stabilized high power diode laser (model SDL-8530: 300-mW output power, 785-nm emission wavelength) from SDL, Inc. (San Jose, Calif.). Raman spectra were collected using a data acquisition package made by EIC, Inc. (Norwood, Mass.) (integration time 120 sec), converted into an ASCII format using GRAMS/32 software (Galactic Industries, Inc.; Salem, N.H.), and analyzed using a chemometrics software package PLS_Toolbox (Version 2.0, Eigenvector Research, Inc., Manson, Wash.) operated with Matlab software (Version 5.3, The Mathworks Inc., Natick, Mass.). Raman spectra were collected using both a standard 5 m long fiber-optic sampling probe and a high temperature probe. The latter was custom-made by InPhotonics, Inc. (Norwood, Mass.) and has the capability to monitor chemical reactions at temperatures up to 400° C. The probe (3" long×0.25" diameter) is housed in stainless steel outer cover (5" long×0.5" diameter) which is durable and compact. A 10-mm working distance enables the probe to collect Raman spectra non-invasively through the viewing port of a reactor.

EXAMPLE 1

Raman spectroscopy was used for a determination of DPC/BPA stoichiometry in bulk solid melt prepared oligomer. To determine appropriate spectral ranges for quantitative determinations of DPC/BPA ratio, Raman spectra of DPC, BPA, phenol, and polycarbonate (LX) were recorded (FIG. 3). Analysis of pure component spectra identified several Raman bands of DPC and BPA useful for ratiometric determinations of stoichiometry. However, most of these bands heavily overlapped with phenol bands. Bands free from phenol interference were 1113 cm$^{-1}$ (BPA) and 877 cm$^{-1}$ (DPC). Upon oligomerization, these band positions were shifted to 1111 cm$^{-1}$ and 888 cm$^{-1}$. The ratio of the intensities at 888 and 1111 cm$^{-1}$ was used for the development of the univariate calibration model.

Typical Raman spectra of solid melt prepared oligomers with different DPC/BPA ratios are presented in FIG. 4. These spectra were collected using a fiber-optic Raman probe. These spectra were baseline-corrected at 860 and 1050 cm$^{-1}$ and further normalized by the intensity of an isolated band at 1111 cm$^{-1}$.

Univariate calibrations were performed by taking a ratio of peak intensities of chosen Raman bands (888 cm$^{-1}$ and 1111 cm$^{-1}$) after subtracting the background. The ratio of band intensities is typically used for quantitation in Raman spectroscopy (Everall, N. et al., (1999); Al-Khanbashi, A., et al., (1998); Ewing, K. J., et al., *Appl. Opt.* 33:6323–6327 (1994); Ewing, K. J., et al., *Anal. Chim. Acta* 340:227–232 (1997); and Boghosian, S., et al., *Appl. Spectrosc.* 53:565–571 (1999)). The ratiometric approach is immune to the variations in collected Raman signal originated from process (temperature and viscosity changes) and instrumental (laser and detector instability) sources.

For determinations of stoichiometry in solid melt prepared oligomers, each sample was measured at three different spatial locations and the spectra were averaged to reduce point-by-point variation in a given sample. Such an approach is recommended by the ASTM Committee E-13 on Molecular Spectroscopy for quantitative analysis in process applications (ASTM E 1655-97, Standard Practices for Infrared, Multivariate, Quantitative Analysis; ASTM: 1997) and is widely used for measurements of solid samples in the near-IR and mid-IR when only a small portion of a sample is illuminated (Analytical Instrumentation: Practical Guides For Measurement and Control; Sherman, R. E., Ed.; Instrument Society of America: Research Triangle Park, NC (1996)).

Raman spectral ratios were converted into predicted DPC/BPA ratios using simple univariate regression. Accuracy was quantified by three measures: (1) the coefficient of multiple determination $R^2$ which indicates the correlation between the predicted and laboratory DPC/BPA ratios; (2) the 95% confidence interval (CI) from the regression model; and (3) the 95% prediction interval (PI) from the regression model. The three figures of merit (coefficient of multiple determination $R^2$, 95% confidence interval (CI) from the regression model, and 95% prediction interval (PI) from the regression model) were computed using Minitab software. Univariate calibration results of the solid melt prepared oligomer samples are presented in FIG. 5. The $R^2$ value for the univariate model was 93.1%.

Accuracy and precision of determinations was also assessed using a multivariate calibration method, Partial Least-Squares (PLS) regression. The covered spectral range was from 500 to 2000 cm$^{-1}$. This method models the sources of variation in the spectral data that correlate with the sources of variation in the DPC/BPA ratio. To reduce computational requirements on the collected Raman spectra, the PLS modeling was performed on spectra with reduced resolution, as described by Shaffer and Combs (Shaffer, R. E. et al., *NRL Memorandum Report*, 6110-99-8342, (1999)). The filtered, low resolution Raman spectra were then mean-centered prior to the PLS model building. Similar results were found using high resolution data.

PLS models were validated using leave-one-out is cross-validation (CV) (Beebe, K. et al., *Chemometrics: A Practical Guide*, Wiley, New York, N.Y. (1998)) after appropriate preprocessing which included mean-centering prior to the PLS model building. The root mean squared error of cross-validation (RMSECV) was used to estimate the predictive performance of the model for data sets with small number of calibration standards. In these experiments, RMSECV is defined to be the standard deviation of the predicted DPC/BPA ratios minus the laboratory estimated DPC/BPA ratios (i.e. standard deviation of test set residuals). Results of multivariate PLS analysis of the Raman spectra of solid melt prepared oligomers are presented in FIG. 6. A four-factor, PLS regression model accounts for 99.98% of the spectral variance and 99.56% of the DPC/BPA ratio and has an RMSECV of 0.025 (in units of molar ratio). The $R^2$ for the multivariate model was 99.6%.

EXAMPLE 2

A determination of DPC/BPA stoichiometry was also made in bulk molten melt prepared oligomer at 210° C. Quantitation of DPC/BPA was performed using both standard and high temperature fiber-optic Raman probes. The standard probe was positioned at about 7-8 mm from the reactor surface heated up to at 210° C.

The Raman spectra collected with the standard probe are presented in FIG. 7. The lower resolution spectra in this plot were Fourier filtered and interpolated to a point spacing of 6.3 cm$^{-1}$. For this data set, all eight samples were analyzed. Each sample was heated twice and 3 replicate spectra were collected, resulting in a total of 8×2×3=48 spectra available for calibration model development. An inspection of the data revealed multiplicative baseline effects that were reduced using multiplicative scatter correction (MSC) (Beebe, K. et al. (1998)).

The results from the PLS calibration model are presented in FIG. 8. In this calibration model, four PLS factors were used which accounted for 98.61% of the spectral variance and 97.07% of the DPC/BPA ratio variance. The $R^2$ for this model was 97.1% and had an RMSECV of 0.0191 (in units of molar ratio).

FIG. 10 presents a plot of the PLS regression vector for the molten melt prepared samples collected with the standard Raman probe. Strong positive regression coefficients can be found at ~888 cm$^{-1}$ which coincide with the strong Raman band from DPC, and at ~1000 cm$^{-1}$ due to a combination of DPC and phenol. Strong negative coefficients at ~835 cm$^{-1}$ are apparently due to both phenol and BPA. The 1111 cm$^{-1}$ spectral band from BPA also has a large negative coefficient. Thus, the general trend observed in this experiment is that BPA contributions provide negative loading and DPC contributions are primarily positive loadings. PLS implicitly subtracted out the contribution of the major interfering peaks due to phenol.

Figure 11:
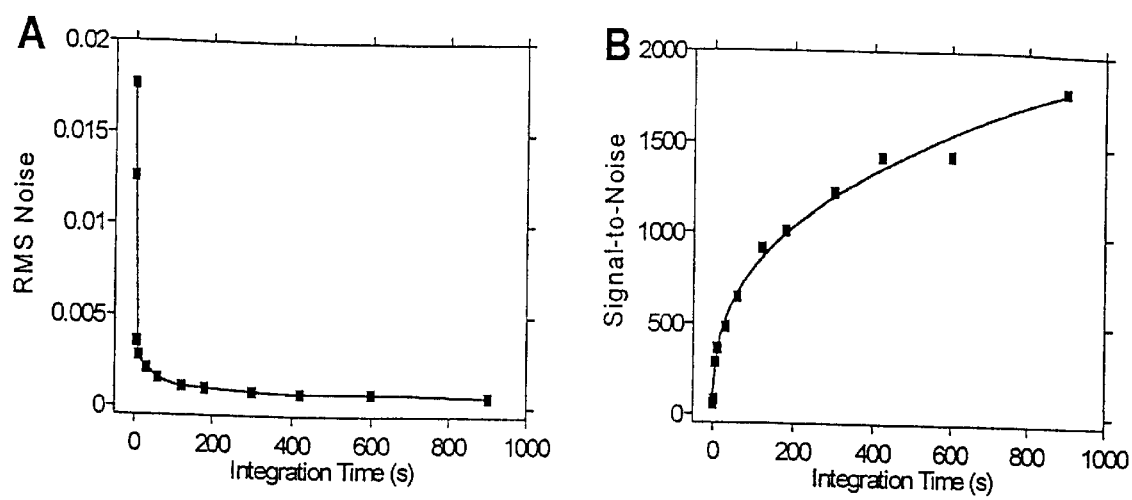
FIG. 11 illustrates an aspect of an embodiment of the invention comprising the quality of Raman signal from an melt prepared oligomer as a function of integration time, wherein (A) shows the root-mean-square (RMS) noise of Raman spectrum measured over the 1050.3 to 1060.1 $cm^{-1}$ region and (B) shows the signal-to-noise ratio for the Raman band (886.56 to 888.13 $cm^{-1}$) used for univariate calibration.

Noise adds to the uncertainty of measurement. Generally, the signal-to-noise ratio (S/N) is the reciprocal of the relative standard deviation (S/N=[RSD]$^{-1}$) (Ingle, J. D. et al., *Spectrochemical Analysis*, Prentice Hall, Englewood Cliffs, N.J. (1988)). FIG. 11 shows the dependence of noise and signal-to-noise ratio (S/N) of the Raman signal of melt prepared oligomers collected with the high temperature probe on integration time. FIG. 11A shows the root-mean-square (RMS) of Raman spectrum measured over the 1050.3–1060.1 cm$^{-1}$ region. FIG. 11B shows the signal-to-noise ratio for the Raman band (888.56–888.13 cm$^{-1}$) used for univariate calibration. The sample measured was a known oligomer (sample #1474) with a DPC/BPA ratio of 1.185. Generally, the high temperature Raman probe provided a signal-to-noise ratio (S/N) of 900 (RSD=~0.1%) in determinations of DPC/BPA ratio using the Raman bands for univariate analysis. It can be seen that to achieve a relative standard deviation (RSD) of 0.7% (S/N=~150) needed for adequate determinations of DPC/BPA ratio, the Raman spectra can be collected with an integration time of as short as 5 sec (FIG. 11).

Determinations of DPC/BPA ratio in the molten melt prepared oligomers were performed with the high temperature Raman probe using five samples. For multivariate analysis, two replicates were analyzed, resulting in 10 spectra for calibration model development and testing. In the PLS calibration model developed for the high temperature Raman probe (see FIG. 9), two PLS factors were used that accounted for 90.31% of the spectral variance and 98.42% of the DPC/BPA ratio variance. The $R^2$ for this model was 98.4% and had a RMSECV of 0.0405 (in units of molar ratio).

The precision of Raman measurements of DPC/BPA ratio in molten oligomers was evaluated for both types of probes. Table 2 summarizes the results of repetitive measurements (n=3) for several samples.

TABLE 2

Precision (% RSD) of Raman Measurements of DPC/BPA Ratio in Molten Oligomers

| Raman Probe Design | Sample 1473 | Sample 1446 | Sample 1444 |
| --- | --- | --- | --- |
| Standard | 1.69 | 2.23 | 0.67 |
| High Temperature | 1.70 | 1.79 | 1.46 |

It will be recognized by those in the art that advantages of the Raman spectroscopy method disclosed here over other methods for the screening of potential reaction conditions include:
1. Qualitative and quantitative assessment of the stoichiometry of reaction components;
2. A method for real-time, on-line assessment of the stoichiometry of reaction components during polymer synthesis;

3. Safe, non-invasive measurements;
4. Nondestructive methods allowing measurements to be performed without destruction of sample and without generation of environmentally hazardous waste;
5. High-throughput analysis capable of automation for combinatorial chemistry or production-scale applications;
6. Analysis of solid or molten samples.

It will be understood that each of the elements described above, or two or more together, may also find utility in applications differing from the types described herein. While the invention has been illustrated and described as embodied as a method for safe, high-throughput, nondestructive analysis of the stoichiometric changes in reaction components during the course of polymer synthesis, it is not intended to be limited to the details shown, since various modifications and substitutions can be made without departing in any way from the spirit of the present invention. For example, robotics equipment can be used to prepare the samples and various types of parallel analytical screening methods can be incorporated. Also, it is contemplated that other components besides BPA and DPC can be measured, including other properties of the sample. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A method for monitoring the process of polymer formation comprising:
   irradiating a polycarbonate or an intermediate thereof with a substantially monochromatic radiation;
   collecting a Raman spectrum corresponding to radiation scattered from the irradiated polycarbonate or intermediate thereof;
   monitoring at least one wavenumber of the Raman spectrum;
   correlating the monitored spectrum to at least one reaction component of interest; and
   applying a predetermined selection test to determine whether any one of a set of preselected reaction components needs to be adjusted.

2. The method of claim 1, wherein the polycarbonate or intermediate thereof is melt polycarbonate.

3. The method of claim 2, wherein the melt polycarbonate is molten.

4. The method of claim 2, wherein the melt polycarbonate is solid.

5. The method of claim 1, wherein a reaction component of interest comprises diphenylcarbonate (DPC).

6. The method of claim 1, wherein a reaction component of interest comprises bisphenol-A (BPA).

7. The method of claim 1, wherein a reaction component of interest comprises polycarbonate product.

8. The method of claim 1, wherein a reaction component of interest comprises phenol.

9. The method of claim 1, further comprising monitoring the Raman spectrum at more than one wavenumber and correlating the Raman spectrum to the ratio of two reaction components of interest.

10. The method of claim 9, wherein the two reaction components of interest comprise diphenylcarbonate (DPC) and bisphenol-A (BPA).

11. The method of claim 9, further comprising univariate analysis for quantitative prediction of the ratio of two reaction components of interest.

12. The method of claim 9, further comprising multivariate analysis for quantitative prediction of the ratio of two reaction components of interest.

13. The method of claim 1, wherein the irradiating light comprises a wavelength in the range of about 400 to 1200 nm.

14. The method of claim 1, wherein the irradiating light comprises a wavelength in the range of about 650 to 900 nm.

15. The method of claim 1, wherein the irradiating light comprises a wavelength in the range of about 750 to 800 nm.

16. The method of claim 1, wherein the irradiating light comprises a wavelength of about 785 nm.

17. The method of claim 1, wherein the collected spectrum comprises wavenumbers in the range of about 50 to 5,000 $cm^{-1}$.

18. The method of claim 1, wherein the collected spectrum comprises wavenumbers in the range of about 200 to 3,500 $cm^{-1}$.

19. The method of claim 1, wherein the collected spectrum comprises wavenumbers in the range of about 400 to 3,000 $cm^{-1}$.

20. The method of claim 1, wherein the collected spectrum comprises wavenumbers in the range of about 500 to 2,000 $cm^{-1}$.

21. The method of claim 1, wherein irradiation and collection of Raman spectra is performed on combinatorial libraries of samples.

22. Computer readable media comprising software code for performing the method of claim 1.

23. A method for monitoring polycarbonate formation comprising:
   irradiating at least one polymer with substantially monochromatic radiation;
   collecting a Raman spectrum corresponding to radiation scattered from the irradiated polymer;
   measuring the intensity of at least two preselected Raman bands;
   correlating the intensity of at least two preselected Raman bands to the stoichiometry of sample diphenylcarbonate (DPC) and bisphenol-A (BPA); and
   applying a predetermined selection test to determine whether the input of DPC and BPA needs to be adjusted.

24. The method of claim 23, wherein the polymer is melt polycarbonate.

25. The method of claim 24, wherein the melt polycarbonate is molten.

26. The method of claim 24, wherein the melt polycarbonate is solid.

27. The method of claim 23, further comprising univariate analysis for correlating the intensity of the preselected Raman bands to the stoichiometry of sample DPC and BPA.

28. The method of claim 23, further comprising multivariate analysis for correlating the intensity of the preselected Raman bands to the stoichiometry of sample DPC and BPA.

29. The method of claim 23, wherein the irradiating light comprises a wavelength in the range of about 400 to 1200 nm.

30. The method of claim 23, wherein the irradiating light comprises a wavelength in the range of about 650 to 900 nm.

31. The method of claim 23, wherein the irradiating light comprises a wavelength in the range of about 750 to 800 nm.

32. The method of claim 23, wherein the irradiating light comprises a wavelength of about 785 nm.

33. The method of claim 23, wherein the collected spectrum comprises wavenumbers in the range of about 50 to 5,000 $cm^{-1}$.

34. The method of claim 23, wherein the collected spectrum comprises wavenumbers in the range of about 200 to 3,500 cm$^{-1}$.

35. The method of claim 23, wherein the collected spectrum comprises wavenumbers in the range of about 400 to 3,000 cm$^{-1}$.

36. The method of claim 23, wherein the collected spectrum comprises wavenumbers in the range of about 500 to 2,000 cm$^{-1}$.

37. The method of claim 23, wherein irradiation and collection of Raman spectra is performed on combinatorial libraries of samples.

38. Computer readable media comprising software code for performing the method of claim 23.

39. An apparatus for the nondestructive monitoring of polymer formation comprising:

a light source, wherein said light source emits substantially monochromatic radiation to irradiate a sample of polycarbonate or intermediate thereof;

a probe, wherein said probe transmits light from said light source to irradiate said sample of polycarbonate or intermediate thereof and collects radiation scattered from the irradiated sample corresponding to a Raman spectrum; and a detector, wherein said detector monitors at least one wavenumber of the collected Raman spectrum correlated to at least one reaction component of interest.

40. The apparatus of claim 39, wherein the sample of polycarbonate or intermediate thereof is melt polycarbonate.

41. The apparatus of claim 40, wherein the melt polycarbonate is molten.

42. The apparatus of claims 40, wherein the melt polycarbonate is solid.

43. The apparatus of claim 39, wherein a reaction component of interest comprises diphenylcarbonate (DPC).

44. The apparatus of claim 39, wherein a reaction component of interest comprises bisphenol-A (BPA).

45. The apparatus of claim 39, wherein a reaction component of interest comprises polycarbonate product.

46. The apparatus of claim 39, wherein a reaction component of interest comprises phenol.

47. The apparatus of claim 39, wherein the irradiating light comprises a wavelength in the range of about 400 to 1200 nm.

48. The apparatus of claims 39, wherein the irradiating light comprises a wavelength in the range of about 650 to 900 nm.

49. The apparatus of claim 39, wherein the irradiating light comprises a wavelength in the range of about 750 to 800 nm.

50. The apparatus of claim 39, wherein the irradiating light comprises a wavelength of about 785 nm.

51. The apparatus of claim 39, wherein the monitored spectrum comprises wavenumbers in the range of about 50 to 5,000 cm$^{-1}$.

52. The apparatus of claim 39, wherein the monitored spectrum comprises wavenumbers in the range of about 200 to 3,500 cm$^{-1}$.

53. The apparatus of claim 39, wherein the monitored spectrum comprises wavenumbers in the range of about 400 to 3,000 cm$^{-1}$.

54. The apparatus of claim 39, wherein the monitored spectrum comprises wavenumbers in the range of about 500 to 2,000 cm$^{-1}$.

55. The apparatus of claim 39, wherein irradiation and collection of Raman spectra is performed on combinatorial libraries of samples.

56. The apparatus of claim 39, further comprising computer readable media software code.

57. A method for monitoring polycarbonate formation comprising:

irradiating at least one polymer, or an intermediate thereof, with substantially monochromatic radiation;

collecting a Raman spectrum corresponding to radiation scattered from the irradiated polymer, or intermediate thereof;

measuring the intensity of at least two preselected Raman bands;

correlating the intensity of at least two preselected Raman bands to the stoichiometry of sample diphenylcarbonate (DPC) and bisphenol-A (BPA); and applying a predetermined selection test to determine whether the input of DPC and BPA needs to be adjusted.

58. The method of claim 57, wherein the polymer or intermediate thereof is melt polycarbonate.

59. The method of claim 58, wherein the melt polycarbonate is molten.

60. The method of claim 58, wherein the melt polycarbonate is solid.

61. The method of claim 57, further comprising univariate analysis for correlating the intensity of the preselected Raman bands to the stoichiometry of sample DPC and BPA.

62. The method of claim 57, further comprising multivariate analysis for correlating the intensity of the preselected Raman bands to the stoichiometry of sample DPC and BPA.

63. The method of claim 57, wherein the irradiating light comprises a wavelength in the range of about 400 to 1200 nm.

64. The method of claim 57, wherein the irradiating light comprises a wavelength in the range of about 650 to 900 nm.

65. The method of claim 57, wherein the irradiating light comprises a wavelength in the range of about 750 to 800 nm.

66. The method of claim 57, wherein the collected spectrum comprises wavenumbers in the range of about 50 to 5,000 cm$^{-1}$.

67. The method of claim 57, wherein the collected spectrum comprises wavenumbers in the range of about 400 to 3,000 cm$^{-1}$.

68. The method of claim 57, wherein the collected spectrum comprises wavenumbers in the range of about 500 to 2,000 cm$^{-1}$.

69. The method of claim 57, wherein irradiation and collection of Raman spectra is performed on combinatorial libraries of samples.

70. Computer readable media comprising software code for performing the method of claim 57.

* * * * *